(12) United States Patent
Thompson et al.

(10) Patent No.: US 7,004,964 B2
(45) Date of Patent: Feb. 28, 2006

(54) APPARATUS AND METHOD FOR DEPLOYMENT OF AN ENDOLUMINAL DEVICE

(75) Inventors: Richard Thompson, Houlton, WI (US); Wade Johnson, Minneapolis, MN (US)

(73) Assignee: Scimed Life Systems, Inc., Maple Grove, MN (US)

( * ) Notice: Subject to any disclaimer, the term of this patent is extended or adjusted under 35 U.S.C. 154(b) by 430 days.

(21) Appl. No.: 10/081,636

(22) Filed: Feb. 22, 2002

(65) Prior Publication Data

US 2003/0163189 A1   Aug. 28, 2003

(51) Int. Cl.
*A61F 2/06* (2006.01)
*A61F 11/00* (2006.01)

(52) U.S. Cl. .................... 623/1.11; 606/108
(58) Field of Classification Search ............... 623/1.11; 606/108, 194, 195, 198
See application file for complete search history.

(56) References Cited

U.S. PATENT DOCUMENTS

| | | |
|---|---|---|
| 4,140,126 A | 2/1979 | Choudhury |
| 4,732,152 A | 3/1988 | Wallstén et al. |
| 4,787,899 A | 11/1988 | Lazarus |
| 4,950,227 A | 8/1990 | Savin et al. |
| 5,078,720 A | 1/1992 | Burton et al. |
| 5,122,136 A | 6/1992 | Guglielmi et al. |
| 5,201,757 A | 4/1993 | Heyn et al. |
| 5,354,295 A | 10/1994 | Guglielmi et al. |
| 5,415,664 A | 5/1995 | Pinchuk |
| 5,456,694 A | 10/1995 | Marin et al. |
| 5,480,423 A | 1/1996 | Ravenscroft et al. |
| 5,591,228 A | 1/1997 | Edoga |
| 5,609,627 A | 3/1997 | Goicoechea et al. |
| 5,634,928 A | 6/1997 | Fischell et al. |
| 5,662,675 A | 9/1997 | Polanskyj Stockert et al. |
| 5,683,451 A | 11/1997 | Lenker et al. |
| 5,800,526 A | 9/1998 | Anderson et al. |
| 5,807,101 A | 9/1998 | Scalzo |
| 5,843,164 A | 12/1998 | Frantzen et al. |
| 5,860,998 A | 1/1999 | Robinson et al. |
| 5,980,533 A * | 11/1999 | Holman ........... 623/1.11 |
| 5,989,280 A | 11/1999 | Euteneuer et al. |
| 6,102,942 A | 8/2000 | Ahari |
| 6,168,610 B1 | 1/2001 | Marin et al. |
| 6,183,443 B1 | 2/2001 | Kratoska et al. |

(Continued)

FOREIGN PATENT DOCUMENTS

EP    0 637 454    2/1995

(Continued)

OTHER PUBLICATIONS

International Search Report for corresponding PCT/US03/04662, mail date Jul. 3, 2003.

(Continued)

*Primary Examiner*—Vy Q. Bui
(74) *Attorney, Agent, or Firm*—RatnerPrestia

(57) ABSTRACT

An introducer deploys an endoluminal device in a distal location from a proximal location. The introducer comprises a retrograde portion, an anterograde portion axially moveable relative to the retrograde portion, a shaft having a distal tip and an anterograde sheath attached to the distal tip, and an inflatable balloon mounted radially outside the retrograde portion for anchoring the device during deployment from its proximal end to its distal end. The retrograde portion may comprise bilumen tubing having an external wall, an internal wall that defines a central lumen radially inward of the internal wall, and an annular lumen in fluid communication with the balloon defined between the external wall and the internal wall.

16 Claims, 3 Drawing Sheets

U.S. PATENT DOCUMENTS

| | | | |
|---|---|---|---|
| 6,322,586 B1 * | 11/2001 | Monroe et al. | 623/1.11 |
| 6,468,244 B1 * | 10/2002 | Leone et al. | 604/103.02 |
| 6,544,223 B1 * | 4/2003 | Kokish | 604/103.01 |
| 6,613,075 B1 * | 9/2003 | Healy et al. | 623/1.11 |
| 2001/0044648 A1 | 11/2001 | Wolinsky et al. | |

FOREIGN PATENT DOCUMENTS

| | | |
|---|---|---|
| EP | 0 684 022 | 11/1995 |
| WO | WO 96/24308 | 8/1996 |
| WO | WO 98/09583 | 3/1998 |
| WO | WO 98/53761 | 12/1998 |
| WO | WO-99/47075 | 9/1999 |
| WO | WO-99/49812 | 10/1999 |
| WO | WO 01/10345 A1 | 2/2001 |

OTHER PUBLICATIONS

U.S. Appl. No. 09/442,165, filed Nov. 16, 1999 to Choulnard et al.

U.S. Appl. No. 09/442,192, filed Nov. 16, 1999 to Zarbatany et al.

U.S. Appl. No. 09/574,418, filed May 19, 2000 to Sullivan et al.

U.S. Appl. No. 09/852,524, filed May 10, 2001 to Elliott.

U.S. Appl. No. 10/080,791, filed Feb. 22, 2002 to Haverkost et al.

U.S. Appl. No. 10/081,641, filed Feb. 22, 2002 to Haverkost et al.

* cited by examiner

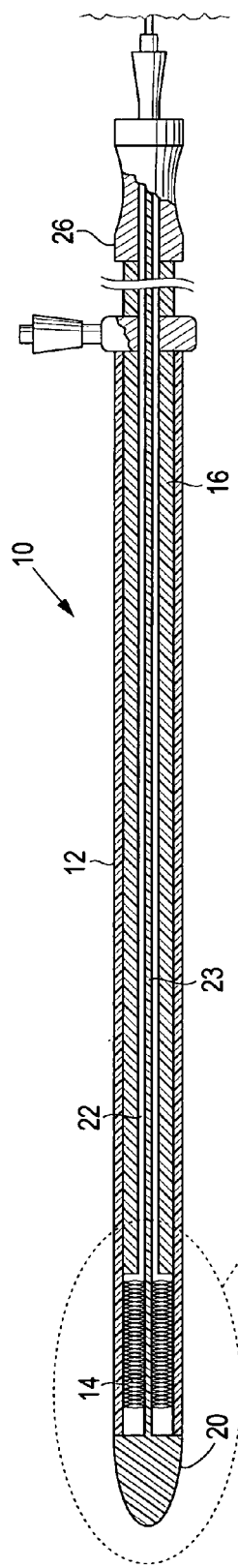
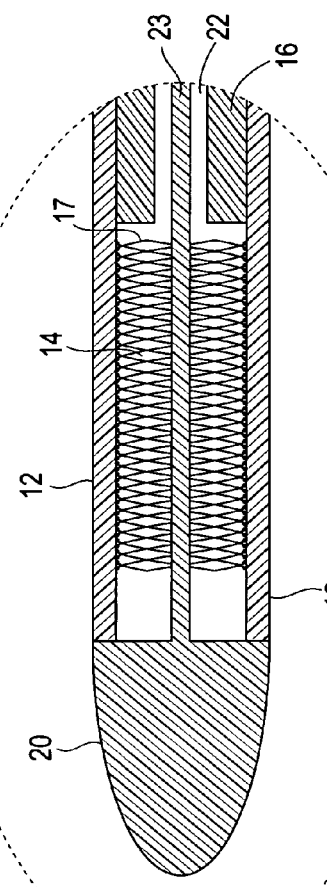
FIG. 1A
PRIOR ART
FIG. 1B
PRIOR ART

APPARATUS AND METHOD FOR DEPLOYMENT OF AN ENDOLUMINAL DEVICE

TECHNICAL FIELD

This invention relates generally to endoluminal devices and, more specifically, to methods and apparatus for deploying endoluminal devices in body lumens.

BACKGROUND OF THE INVENTION

A stent is an elongated device used to support an intraluminal wall. In the case of a stenosis, a stent provides an unobstructed conduit through a body lumen in the area of the stenosis. Such a stent may also have a prosthetic graft layer of fabric or covering lining the inside and/or outside thereof. Such a covered stent is commonly referred to in the art as an intraluminal prosthesis, an endoluminal or endovascular graft (EVG), or a stent-graft. A stent-graft may be used, for example, to treat a vascular aneurysm by removing the pressure on a weakened part of an artery so as to reduce the risk of rupture. Other devices, such as filters, particularly vena cava filters, may have similar structures to stents and may be placed in a body lumen by similar methods. As used herein, the term "endoluminal device" refers to covered and uncovered stents, filters, and any other device that may be placed in a lumen. The term "stent" as used herein is a shorthand reference referring to a covered or uncovered stent.

Typically, an endoluminal device, such as a stent-graft deployed in a blood vessel at the site of a stenosis or aneurysm, is implanted endoluminally, i.e. by so-called "minimally invasive techniques" in which the device, restrained in a radially compressed configuration by a sheath or catheter, is delivered by a delivery system or "introducer" to the site where it is required. The introducer may enter the body from an access location outside the body, such as through the patient's skin, or by a "cut down" technique in which the entry blood vessel is exposed by minor surgical means. The term "proximal" as used herein refers to portions of the stent or delivery system relatively closer to this access location, whereas the term "distal" is used to refer to portions farther from the access location.

When the introducer has been threaded into the body lumen to the stent deployment location, the introducer is manipulated to cause the stent to be ejected from the surrounding sheath or catheter in which it is restrained (or alternatively the surrounding sheath or catheter is retracted from the stent), whereupon the stent expands to a predetermined diameter at the deployment location, and the introducer is withdrawn. Stent expansion may be effected by spring elasticity, balloon expansion, or by the self-expansion of a thermally or stress-induced return of a memory material to a pre-conditioned expanded configuration.

Referring now to a typical prior art introducer as seen in FIGS. 1A and 1B, there is shown a standard pre-loaded delivery system 10 comprising an outer sheath 12, a compressed endoluminal device 14 loaded therein, and a conventional stabilizer 16 loaded adjacent to the proximal end 17 of the endoluminal device. A standard deployment technique comprises maneuvering the introducer to a desired deployment location and retracting outer sheath 12 so that the endoluminal device is deployed beginning at its distal end and ending at its proximal end. Stabilizer 16 stabilizes or prevents retraction of endoluminal device 14 when sheath 12 is retracted, thus effecting deployment of the device into a desired location by forcing relative movement between the sheath and the device.

Delivery system 10 also may comprise a catheter tip 20 at its distal end attached to an internal shaft 23 that runs through the delivery system through inner lumen 22 in stabilizer 16, as shown in FIG. 1A. A stabilizer handle 26 is typically located at the proximal end of stabilizer 16, outside the body lumen. Internal shaft 23 may guide the delivery system through the body lumen over a guidewire (not shown) to the area to be repaired, or may be adapted for inflating a balloon (if applicable), and/or for flushing the system.

It is often important during endoluminal device delivery to ensure accurate placement of the device termini, particularly in intravascular deployment of multipart stents. Improper stent placement can prevent successful medical treatment. There is a particular need in the art to anchor the proximal end of a self-expanding stent while deploying the distal end, and also to provide accurate deployment of self-expanding stents in a way that prevents recoil of the endoluminal device upon release, which may adversely affect the accuracy of the device placement.

In a procedure to repair an abdominal aortic aneurysm (AAA), use of a modular self-expanding stent involves accurate placement of a terminus of a first stent component in the abdominal aorta just below the renal arteries. A second stent component is then deployed in the first stent component and permitted to extend to a terminus in one of the iliac arteries. It is difficult, however, to ensure accurate placement of the iliac terminus of the second stent component. If the terminus is not placed far enough into the iliac, then the stent may be ineffective. If the terminus extends too far, it may interfere with blood flow in arteries branching from the iliac, such as the internal iliac artery. This problem also occurs in the deployment of multipart stents in other branched arteries. Thus, it is particularly desirable to provide a way to ensure accurate deployment of all the termini of a multipart stent.

SUMMARY OF THE INVENTION

In accordance with this invention, there is provided an introducer having a retrograde portion and an anterograde portion axially moveable relative to one another. An inflatable balloon is provided radially outside the distal end of the retrograde portion, such as for anchoring the endoluminal device during deployment of the endoluminal device from the device proximal end to the device distal end. The anterograde portion comprises a distal tip and an anterograde sheath attached proximally to the distal tip. A shaft is attached to the distal tip and extends concentrically through a central lumen defined by the anterograde portion and retrograde portion, such as for moving the anterograde portion relative to the retrograde portion. The endoluminal device is mounted concentrically over the shaft in the central lumen and has a distal end contained by the anterograde portion and a proximal end contained by the retrograde portion.

The retrograde portion may comprise bitumen tubing having an external wall, an internal wall that defines the central lumen radially inward of the internal wall, and an annular lumen defined between the external wall and the internal wall. The annular lumen is in fluid communication with the balloon, which is located radially outward of the external wall at or near a distal end of the retrograde portion.

The invention also comprises a method for deployment of an endoluminal device in a distal location in a body lumen from a proximal location. The method comprises the steps of inserting an introducer of the present invention into a body lumen, aligning the proximal end of the endoluminal device in a deployment location, and retracting the retrograde portion to deploy the proximal portion of the endoluminal device including the proximal end. The retrograde portion of the introducer is then advanced so that the inflatable balloon is aligned axially within the proximal portion of the endoluminal device. The balloon is inflated to compress the endoluminal device against the lumen wall while the shaft is extended to distally advance the anterograde sheath to deploy a remaining portion of the endoluminal device.

It is to be understood that both the foregoing general description and the following detailed description are exemplary, but not restrictive, of the invention.

BRIEF DESCRIPTION OF THE DRAWING

The invention is best understood from the following detailed description when read in connection with the accompanying drawing, in which:

FIG. 1A shows a longitudinal section of a standard introducer of the prior art;

FIG. 1B shows a detailed longitudinal section of the encircled portion of FIG. 1A.;

DETAILED DESCRIPTION OF THE INVENTION

The invention will next be illustrated with reference to the figures wherein the same numbers indicate similar elements in all figures. Such figures are intended to be illustrative rather than limiting and are included herewith to facilitate the explanation of the apparatus of the present invention.

Figure 2A:
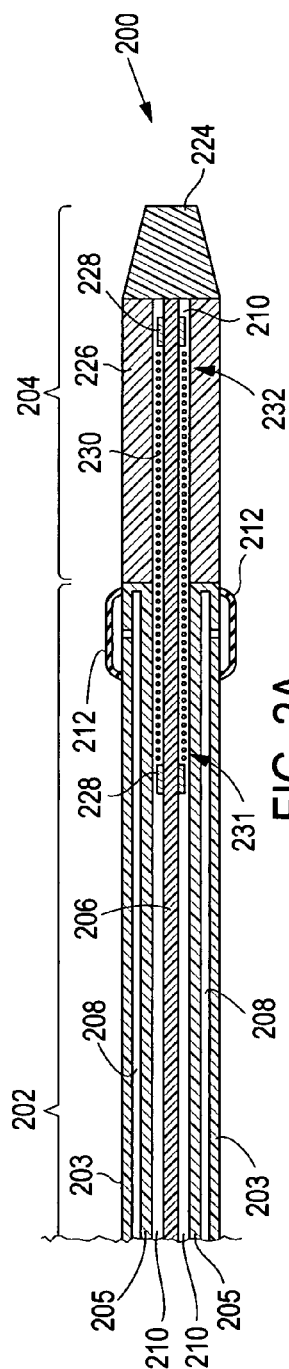
FIG. 2A shows a longitudinal section of an exemplary introducer of the present invention.
Figure 2B:
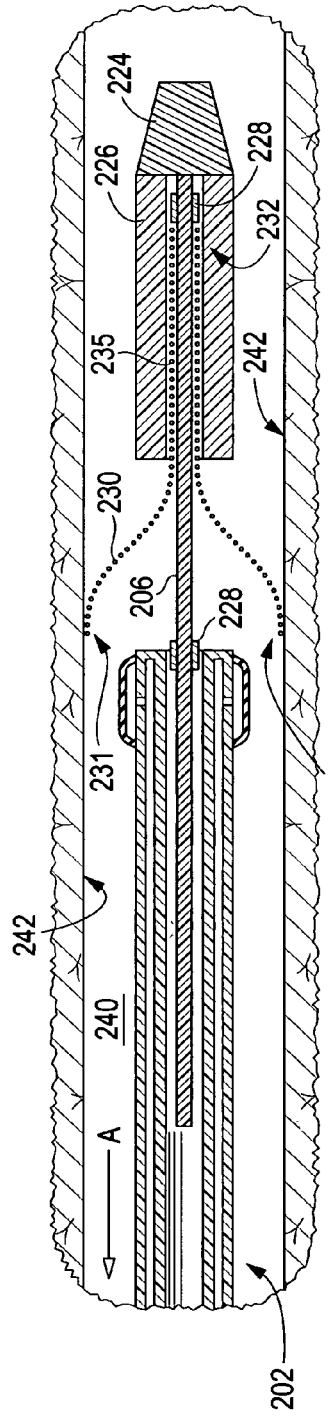
FIG. 2B shows a longitudinal section of the introducer of FIG. 2A in mid-deployment of an endoluminal device.
Figure 2C:
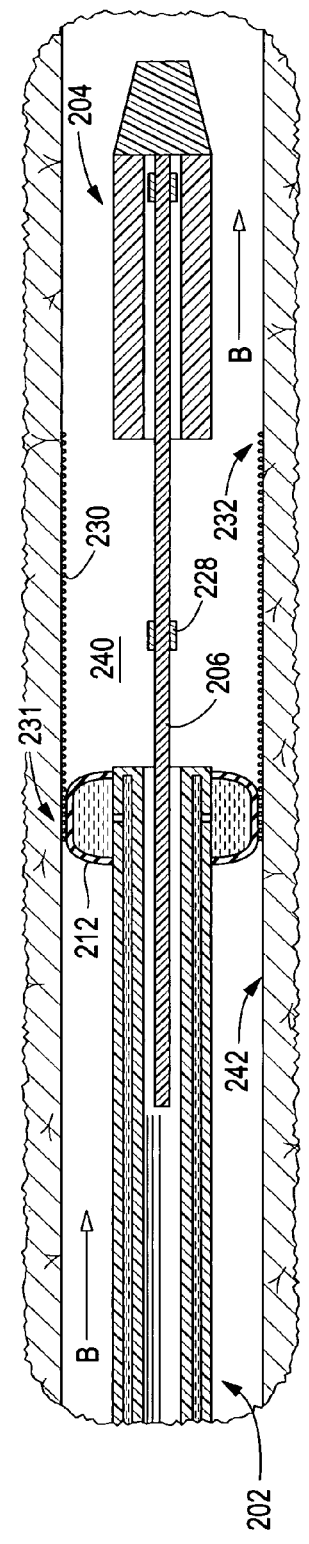
FIG. 2C shows a longitudinal section of the introducer of FIG. 2A after deployment of the endoluminal device.

Referring now to FIGS. 2A–C there is shown an exemplary introducer embodiment 200 in accordance with the present invention. Retrograde portion 202 of introducer 200 comprises bitumen tubing having an exterior wall 203, an interior wall 205, an annular lumen 208 defined by the space between the interior wall and the exterior wall, and a central lumen 210 radially inward of the interior wall. Balloon 212 is located at or near the distal end of exterior wall in fluid communication with annular lumen 208, allowing fluid to flow through the annular lumen to inflate the balloon when desired. Anterograde portion 204 of introducer 200 is attached to shaft 206 and comprises distal tip 224 attached to anterograde sheath 226, which further defines an anterograde portion of central lumen 210. Shaft 206 may have one or more radiopaque markers 228, one shown in FIG. 2A adjacent the proximal end 231 and another shown adjacent the distal end 232 of the endoluminal device 230, which is contained within central lumen 210.

Figure 3:
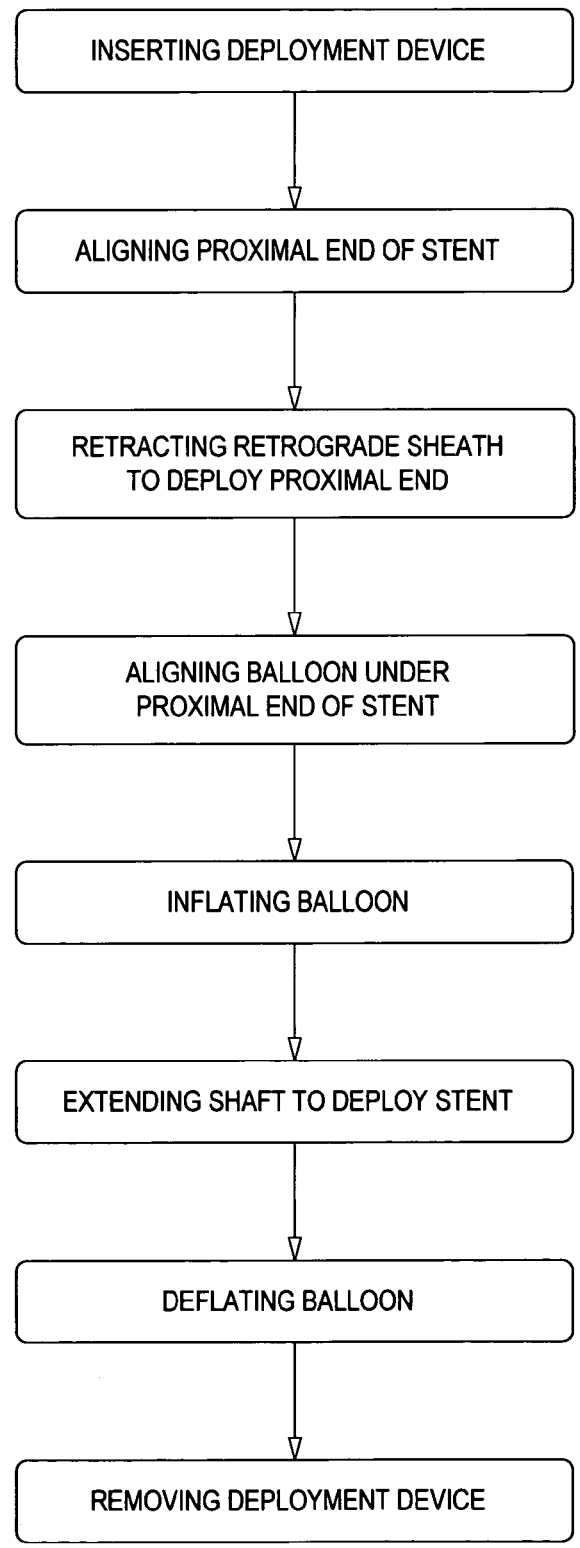
FIG. 3 depicts a flowchart of an exemplary method of deploying an endoluminal device using the introducer of the present invention.

An exemplary method for using introducer 200 is depicted in the flowchart shown in FIG. 3. The method may be performed, for example, in an operating room or an angiographic suite, preferably under fluoroscopic guidance as is known in the art. First, introducer 200 is inserted into a body lumen 240, as indicated in step 310, distal tip 224 first, from a proximal access site (not shown), such as a femoral artery or iliac artery for vascular deployment. Typically, introducer 200 is threaded into the lumen over a guidewire (not shown) as is well known in the art. The access site may be surgically exposed and punctured with, for example, an 18-gauge needle as is known in the art.

Next, in step 320, the proximal end 231 of endoluminal device 230 is aligned in an appropriate deployment position. Fluoroscopic guidance, such as by using radiopaque markers 228 and/or a guide wire, may be used to guide proximal end 231 into the desired position. For example, where endoluminal device 230 is an AAA stent graft, proximal end 231 of device 230 is positioned in the iliac (not shown) artery, preferably just above a branch of the internal iliac artery (not shown). Although illustrated herein with respect to a self-expanding stent, the endoluminal device may comprise any device for placement in a lumen, including but not limited to stents, grafts, combinations thereof, and filters, such as vena cava filters.

After end 231 is aligned in the desired position, retrograde sheath 202 is retracted in the direction of arrow A as shown in FIG. 2B, at least far enough to expose proximal section 231 of device 230, allowing it to expand against the lumen wall 242, as indicated in step 330. Then, retrograde portion 202 is advanced in the direction of arrow B so that balloon 212 is aligned under proximal section 231 of device 230, as indicated in step 335 and as shown in FIG. 2C. Balloon 212 is inflated in step 340, by pressurizing the balloon with fluid communicated through annular lumen 208, to exert radial force that presses the proximal section 231 of device 230 against the lumen wall 242.

In step 350, shaft 206 is extended distally to advance anterograde portion 204 of introducer 200 to deploy anterograde portion 235 of device 230 as shown in FIG. 2C. As used herein, the "retrograde portion" of device 230 refers to any portion initially covered by the retrograde sheath, and the "anterograde portion" of device 230 refers to the remainder of the device distal of the retrograde portion. Prior to extending the shaft, the guidewire and retrograde portion 202 of introducer 200 may typically be locked together to prevent movement of the retrograde sheath or the guidewire during extension of the shaft. After anterograde portion 235 has been deployed, balloon 212 is then deflated as indicated in step 360, anterograde portion 204 and retrograde portion 202 brought together again abutting one another, and introducer 200 removed from the lumen in accordance with step 370. If desired, prior to removal from the lumen, balloon 212 may be used for modeling device 230 to better conform to the contours of the lumen wall 242, as is known in the art. Thus, introducer 200 and the method depicted in FIG. 3 provides means for accurately placing the proximal end of an endoluminal device.

Although depicted in FIGS. 2A–2C with the anterograde portion 204 and retrograde portion 202 extending approximately equally over the length of device 230, in many embodiments the length of the anterograde portion over the device is longer than the length of the retrograde portion over the device. Retrograde portion 202 may typically only be long enough so that when proximal end 231 of device 230 is deployed by retracting retrograde portion 202, the deployed length of the device proximal end is sufficient to be engaged by balloon 212 against body lumen 242.

One concern of the reverse deployment method and introducers described herein for deployment of AAA stent-grafts, is that if anterograde portion 204 is too long, the anterograde portion may enter the heart during the advancement step. Other, non-AAA applications may have similar concerns with surrounding organs or other body structure. Thus, the dimensions of the introducer may be optimized to prevent damage caused by anterograde portion 204 being too long. One way of shortening anterograde portion 204 for a particular application is to lengthen retrograde portion 202. Thus, in some embodiments, retrograde portion 202 may be longer than just an effective amount to provide a sufficiently long deployed proximal portion 231 of device 230 for engagement by balloon 212, including embodiments where anterograde portion 204 and the retrograde portion are equal, or where the anterograde portion is longer than the retrograde portion. Embodiments having retrograde and anterograde portions of approximately equal length may be useful where the location of the proximal end of the device is less important than aligning the middle of the device with a certain region of a lumen.

Although depicted herein with a retrograde portion comprising coaxial bilumen tubing, the introducer of the present invention may comprise other structures that provide a balloon radially outside the retrograde portion. For example, the bitumen tubing may not comprise coaxial tubing, but rather tubing wherein the central lumen and the lumen in fluid communication with the balloon are side-by-side or in some other configuration. The longitudinal sectional view of such a configuration would be similar to FIG. 2A except that the upper longitudinal section of lumen 108 would be the entire lumen and there would be no bottom section of that lumen. Other embodiments may also be provided within the scope of this invention.

Although illustrated and described herein with reference to certain specific embodiments, the present invention is nevertheless not intended to be limited to the details shown. Rather, various modifications may be made in the details within the scope and range of equivalents of the claims and without departing from the spirit of the invention.

What is claimed:

1. An introducer for deployment of an endoluminal device in a distal location inside a body lumen from a proximal location outside the body lumen, the introducer comprising:
    a retrograde portion;
    an anterograde portion, axially moveable relative to the retrograde portion, comprising a distal tip and an anterograde sheath attached proximally to the distal tip;
    a shaft attached to the distal tip and extending concentrically through a central lumen defined by the anterograde portion and retrograde portion;
    an endoluminal device mounted concentrically over the shaft in the central lumen and having a distal end contained by the anterograde portion and a proximal end contained by the retrograde portion positioned radially outward of the proximal end of the device; and
    an inflatable balloon mounted radially outside the retrograde portion, the balloon positioned to anchor a proximal portion of the endoluminal device against the body lumen during deployment of the device.

2. The introducer of claim 1, wherein the retrograde portion comprises bilumen tubing having an external wall, an internal wall that defines the central lumen radially inward of the internal wall, and an annular lumen defined between the external wall and the internal wall, the annular lumen in fluid communication with the balloon, the balloon located radially outward of the external wall at or near a distal end of the retrograde portion.

3. The introducer of claim 1, wherein the endoluminal device has a length and the balloon has a length that is less than the endoluminal device length.

4. The introducer of claim 1, wherein the retrograde sheath and the anterograde portion axially abut one another.

5. The introducer of claim 1, wherein the retrograde portion extends over a longer portion of the endoluminal device than the anterograde sheath.

6. The introducer of claim 1, wherein the anterograde sheath extends over a longer portion of the endoluminal device than the retrograde portion.

7. The introducer of claim 1, wherein the anterograde sheath and the retrograde portion extend over essentially equal lengths of the endoluminal device.

8. The introducer of claim 1, wherein the shaft comprises one or more radiopaque markers.

9. The introducer of claim 1 further comprising at least a first radiopaque marker that marks the proximal end of the device.

10. The introducer of claim 9 further comprising a second radiopaque marker that marks the distal end of the device.

11. The introducer of claim 1, wherein the endoluminal device comprises a stent, graft, or a combination thereof.

12. The introducer of claim 1, wherein the endoluminal device comprises a vena cava filter.

13. The introducer of claim 1, wherein the endoluminal device comprises a stent-graft for repair of an abdominal aortic aneurysm.

14. The introducer of claim 1, wherein the endoluminal device is self-expanding.

15. The introducer of claim 1, wherein the endoluminal device is adapted for deployment in a location having a sensitive area located distally of the deployment location, the anterograde portion having a length sufficiently short to prevent intrusion of the anterograde portion into the sensitive area.

16. An introducer for deployment of a self-expanding endoluminal device in a distal location inside a body lumen from a proximal location outside the body lumen, the introducer comprising:
    a retrograde portion having a distal end and comprising coaxial bilumen tubing having an external wall, an internal wall, a balloon located radially outward of the external wall at or near the retrograde portion distal end for anchoring the endoluminal device against the body lumen during deployment of the device from the device proximal end to the device distal end, a retrograde central lumen defined radially inward of the internal wall, and an annular lumen defined between the external wall and the internal wall, the annular lumen in fluid communication with the balloon;
    an anterograde portion comprising a distal tip, an anterograde sheath attached proximally to the distal tip, and an anterograde central lumen defined radially inward of the anterograde sheath;
    an endoluminal device mounted concentrically over the shaft in the retrograde and anterograde central lumens, the device distal end contained by the anterograde portion and the device proximal end contained by the retrograde portion, the retrograde portion having a length sufficient to be engaged by the balloon against the lumen wall; and
    a shaft attached to the distal tip and extending concentrically through the anterograde and retrograde central lumens, the shaft comprising at least a first radiopaque marker that marks the proximal end of the endoluminal device and adapted for moving the anterograde portion relative to the retrograde portion.

* * * * *